United States Patent [19]

Patrick

[11] 4,121,340
[45] Oct. 24, 1978

[54] ORAL IMPLANTOLOGY

[76] Inventor: Daniel R. Patrick, 5601 Four Mile Dr., Kokomo, Ind. 46901

[21] Appl. No.: 749,532

[22] Filed: Dec. 10, 1976

[51] Int. Cl.² .............................................. A61C 8/00
[52] U.S. Cl. ................................................. 32/10 A
[58] Field of Search ....................................... 32/10 A

[56] References Cited

U.S. PATENT DOCUMENTS

| | | | |
|---|---|---|---|
| 3,082,525 | 3/1963 | Christensen | 32/10 A |
| 3,579,829 | 5/1971 | Sampson | 32/10 A |
| 3,977,081 | 8/1976 | Zambelli et al. | 32/10 A |

Primary Examiner—Louis G. Mancene
Assistant Examiner—John J. Wilson
Attorney, Agent, or Firm—George H. Mitchell, Jr.

[57] ABSTRACT

A combination bladevent subperiosteal implant in which the abutment post which bears an artificial tooth or a tooth in a full arch splint is isolated from and only indirectly attached to the bladevent body through a subperiosteal portion of the implant. The combination implant has a shallower sulcus depth and less epithelial invagination.

7 Claims, 4 Drawing Figures

ORAL IMPLANTOLOGY

BACKGROUND OF THE INVENTION

Oral implantation devices are well known in the art and a pertinent example of the prior art is U.S. Pat. No. 3,465,441, issued Sept. 9, 1969, to Linkow. This patent depicts several embodiments of a bladevent implant on which the abutment post bearing a tooth is directly joined to the bladevent body portion which becomes embedded in the cancellous bone of the jaw.

The present invention has for its objective to improve upon the above prior art arrangement through the provision of a combination type implant having a bladevent body for insertion into the spongy jaw bone and a subperiosteal portion attached to the bladevent portion at two end extremities of the latter only and otherwise isolated therefrom. The abutment post is directly attached at the center of the subperiosteal portion or frame of the implant and is therefore isolated from and only indirectly connected with the bladevent body.

Among the features and advantages of the above combination oral implant are the following.

(1) The blade portion of the implant is completely surrounded by bone except for its two slender end elements which are joined with the opposite end portions of the subperiosteal component of the implant.

(2) All of the subperiosteal portion of the implant lies on top of the bone but below the oral mucosa and periosteum except for the implant abutment post which protrudes into the oral cavity.

(3) A most important distinction between the invention and other oral implants is that the abutment post is not attached directly to the implant blade, but is indirectly attached through the subperiosteal part of the implant, the latter being joined to the blade at two local end points. This permits the bone to grow completely over the top of the blade except at the two small areas where the blade and subperiosteal portions are joined.

(4) An important result of the feature immediately above is that the combination implant can have a shallower sulcus depth and less epithelial invagination. That is, oral epithelium cannot grow down along the implant abutment post and around the blade portion, as opposed to what can take place with implants in which the abutment post is directly attached to the blade portion.

(5) The blade portion of the implant can be placed in the bone at any angle and still have the implant posts parallel to the tooth abutments without bending the neck of the implant.

(6) There is greater vertical and lateral stability for the implant when installed. The combination structure tends to prevent sinking of the blade into the cancellous bone after long term function.

(7) Slightly less vertical alveolar process is required for implant success due to added stability afforded by the subperiosteal framework, making it easier to avoid the mandibular canal or the maxilary sinus.

(8) The head of the combination implant can be positioned mesiodistally exactly where needed for proper occlusion.

Other features and advantages of the invention will become apparent during the course of the following description.

DETAILED DESCRIPTION

Figure 1:
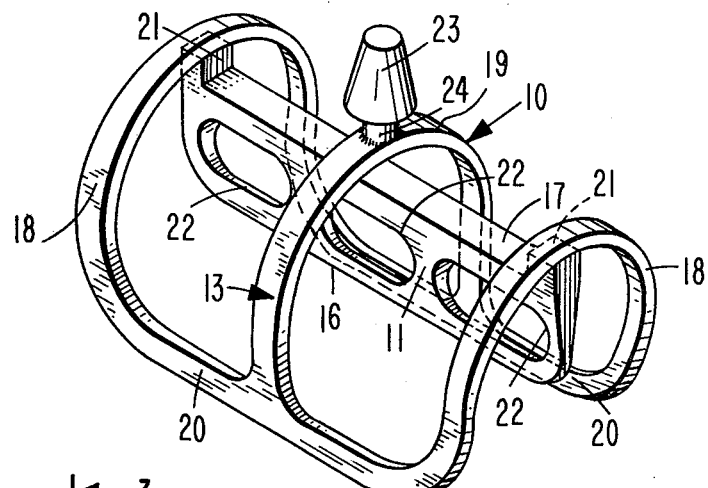
FIG. 1 is a perspective view of a combination oral implant embodying the invention.

Referring to the drawings in detail wherein like numerals designate like parts, the numeral 10 designates an oral implant embodying the invention in its entirety. The implant is a metal centrifugal casting formed preferably from surgical vitallium which is an alloy having the approximate composition by weight:

Co/Cr/Mo/Ni 62/27/5/3.

The implant 10 made from this material must be customized for each dental patient.

The implant 10 is a combination implant having a bladevent body 11 for direct insertion into the cancellous bone structure 12 and a subperiosteal portion or frame 13 which is placed beneath the oral mucosa 14 and the underlying periosteum 15.

The bladevent body 11 is an elongated blade member which tapers to a sharp longitudinal edge 16 along one edge portion, the opposite longitudinal edge portion 17 being blunt. The subperiosteal portion 13 is of generally U-shaped configuration as viewed from the end, including a pair of end frames 18 and an intermediate frame 19, all of the same configuration. These frames 18 and 19 straddle the bladevent body 11 symmetrically so that their opposite approximately vertical sides are spaced equidistantly from the opposite sides of the bladevent body of the implant. The lower ends of the frames 18 and 19 are joined integrally with bottom longitudinal side bars 20 which complete the formation of the subperiosteal element or portion of the implant.

The subperiosteal portion 13 is joined at its opposite ends of the corresponding ends of the bladevent body 11 at the tops and centers of the end frames 18 through short upstanding lugs 21 provided on the bladevent body. The elements are integrally joined at these points only by casting. The bladevent body 11 also preferably has bone growth openings 22 formed therethrough, as shown.

A tapered abutment post 23 is integrally secured to the top and center of the intermediate frame 19 and has a reduced width neck 24 at its lower end, immediately above the frame 19.

A chief feature of the invention is the arrangement whereby the abutment post 23 is not attached directly to the implant bladevent body 11, but is connected indirectly to the blade through the subperiosteal portion or frame 13. This has a number of important advantages which have already been enumerated, including the fact that bone may grow completely over the top of the bladevent body 11 except at the two ends thereof where the subperiosteal frame is attached.

When the combination implant has been installed by known surgical techniques, the bladevent body 11 is firmly anchored in the bone 12 and the relatively wide straddling subperiosteal frame 13 will span the top of the bone structure and the two sides thereof while lying beneath the gingival tissue and the periosteum, as shown. It will lend strength and stability to the entire implant, as previously noted.

Figure 2:
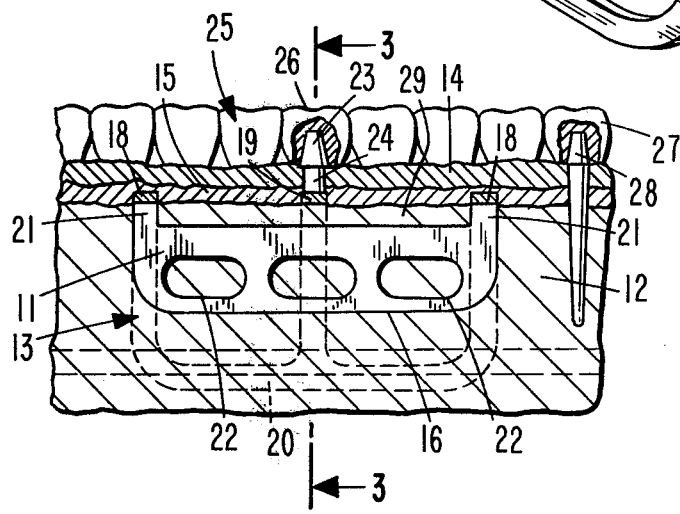
FIG. 2 is a vertical sectional view showing the implant installed.
Figure 3:
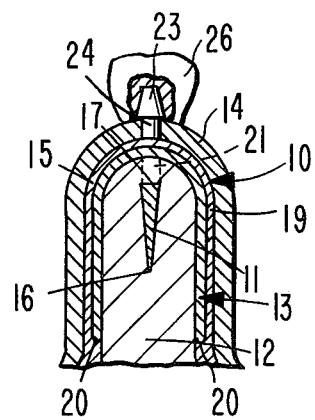
FIG. 3 is a transverse vertical section taken on line 3—3 of FIG. 2.
Figure 4:
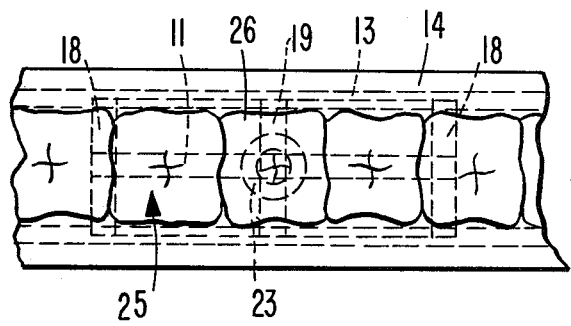
FIG. 4 is a plan view of the installed implant.

When so installed, an acrylic full arch splint 25 may be structurally joined to the combination implant through the abutment post 23 by having one of the artificial teeth 26 of the splint recessed to accept the abutment post and firmly secured thereto by known techniques. The artificial teeth of the splint 25 on opposite sides of the abutment post 23 lie on the gingival tissue, as shown. In FIG. 2, there is also shown another artificial tooth 27 attached to the stub 28 of a natural tooth and forming no part of the present invention.

It may now be understood that with the bladevent body 11 fully and bodily embedded in the bone 12 well below the insertion margin of the bone, the bone in time can grow into the region 29, FIG. 2, above the bladevent body so that the latter will be completely surrounded by bone except at the two small regions occupied by the lugs 21.

In light of the foregoing description and drawings, it is thought that the novel features of the invention over the prior art will now be apparent to those skilled in the art to which this invention pertains.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. An oral implant comprising a bladevent body adapted for insertion bodily into oral bone structure, at least one abutment post external to bone structure and adapted to project into the oral cavity for supporting an artifical tooth therein, and means directly joined to and supporting said abutment post and adapted to lie beneath gingival tissue and the periosteum and external to bone structure and being joined to the bladevent body, said means comprising a downwardly open frame member having sides and a top spaced from and partly surrounding the bladevent body, said frame member being attached at its top and opposite ends only to the top and opposite ends of the bladevent body at a pair of local small regions on the bladevent body and frame member, said abutment post being attached to the top of said frame at a position spaced from said local small regions, whereby the abutment post is isolated from the bladevent body and connected indirectly therewith only through said frame member.

2. An oral implant as defined by claim 1, wherein said bladevent body, said abutment post and said means are integrally cast.

3. An oral implant as defined by claim 2, and wherein said implant is integrally cast from vitallium.

4. An oral implant comprising a bladevent body adapted for insertion in oral bone structure well beneath the periosteum, a subperiosteal frame member straddling the bladevent body and having sides and a top spaced from the bladevent body, said top of the subperiosteal frame member being joined to the bladevent body locally at the ends only of the bladevent body, and an abutment post secured to the top of and rising from the subperiosteal frame member, whereby the abutment post is indirectly joined to the bladevent body through said subperiosteal frame member, said subperiosteal frame member being of inverted U-shaped form and downwardly open between its sides and said sides being equidistantly spaced from opposite sides of the bladevent body, the bladevent body having a substantially sharp longitudinal edge between said sides, said subperiosteal frame member having end and intermediate U-shaped frame sections and lower longitudinal side bars interconnecting said frame sections, said abutment post being secured to the top of said intermediate frame section.

5. An oral implant as defined by claim 4, in which said bladevent body, said subperiosteal frame member and said abutment post are all integrally cast as a unitary body.

6. An oral implant as defined by claim 5, and said implant formed from surgical vitallium or metal of equivalent composition and bio-compatability.

7. An oral implant as defined by claim 4, and said bladevent body joined to said subperiosteal frame member at the tops of said end U-shaped frame sections.

* * * * *